(12) United States Patent
Gill

(10) Patent No.: US 7,351,239 B2
(45) Date of Patent: Apr. 1, 2008

(54) IMPLANTABLE DRUG DELIVERY PUMP

(75) Inventor: Steven Streatfield Gill, Bristol (GB)

(73) Assignee: Renishaw PLC, Gloucestershire (GB)

( * ) Notice: Subject to any disclaimer, the term of this patent is extended or adjusted under 35 U.S.C. 154(b) by 0 days.

(21) Appl. No.: 11/698,571

(22) Filed: Jan. 26, 2007

(65) Prior Publication Data
US 2007/0123843 A1  May 31, 2007

Related U.S. Application Data

(63) Continuation of application No. 10/427,506, filed on Apr. 30, 2003, now abandoned.

(30) Foreign Application Priority Data
Apr. 30, 2002  (GB) ................................ 0209904.2

(51) Int. Cl.
*A61K 9/22* (2006.01)
*A61M 31/00* (2006.01)

(52) U.S. Cl. .............................. 604/890.1; 604/288.01; 604/288.04

(58) Field of Classification Search ................. 604/151, 604/152, 154, 45.01, 95.02, 288.01–288.04, 604/890.1; 417/416, 417, 549, 550
See application file for complete search history.

(56) References Cited

U.S. PATENT DOCUMENTS

| 6,176,242 B1 | 1/2001 | Rise |
| 6,554,822 B1 | 4/2003 | Hoischneider |
| 2002/0013612 A1 | 1/2002 | Whitehurst |
| 2003/0171738 A1 | 9/2003 | Konieczynski |

*Primary Examiner*—Sharon E. Kennedy
(74) *Attorney, Agent, or Firm*—Kohn & Associates, PLLC; Kenneth I. Kohn

(57) ABSTRACT

The pump includes a metering pump including a rotor, at least two lengths of tubing against which the rotor is movable to urge the drug therethrough, and an outlet port associated with each of the at least two lengths of tubing. In this way, a drug may be supplied to more than one neurological target.

20 Claims, 9 Drawing Sheets

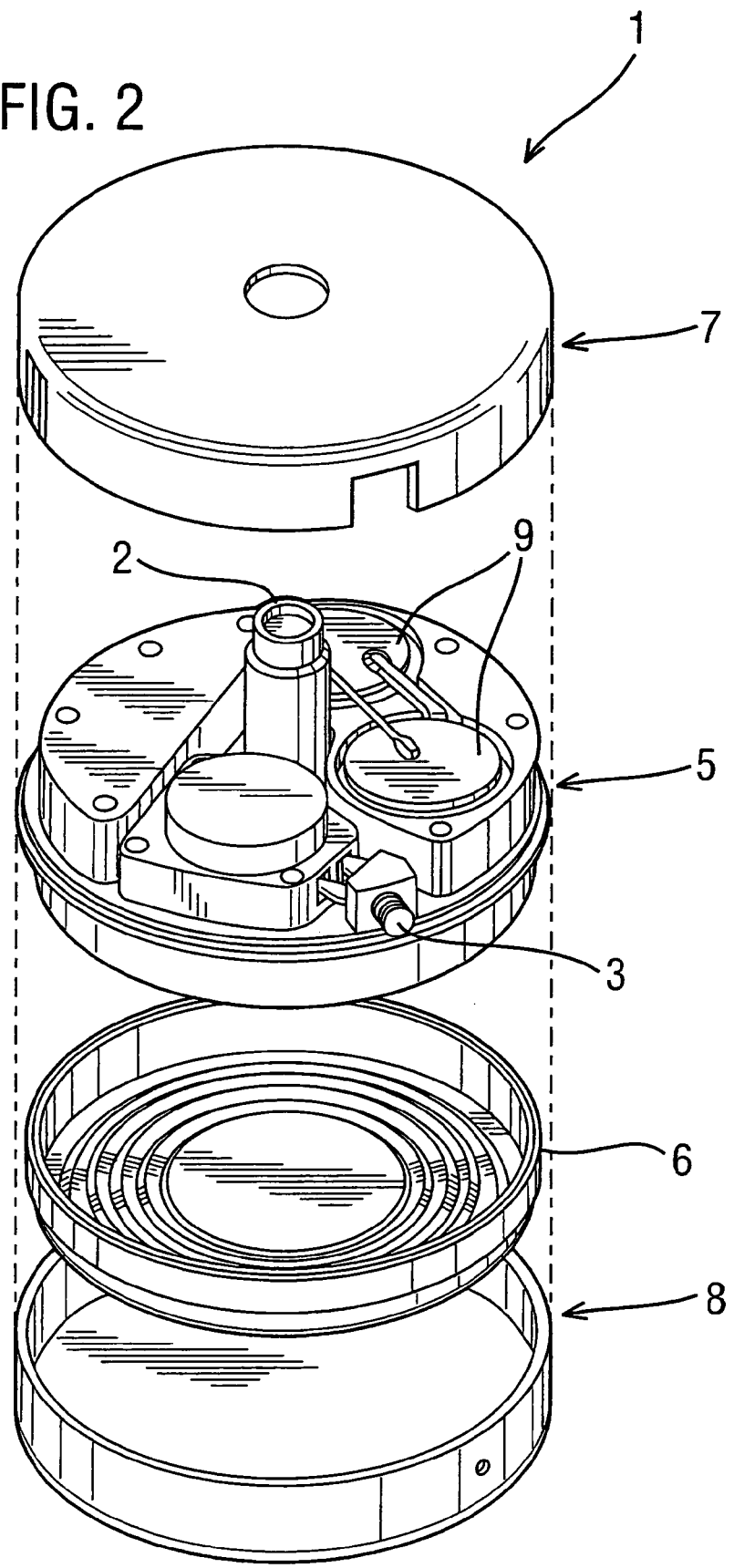

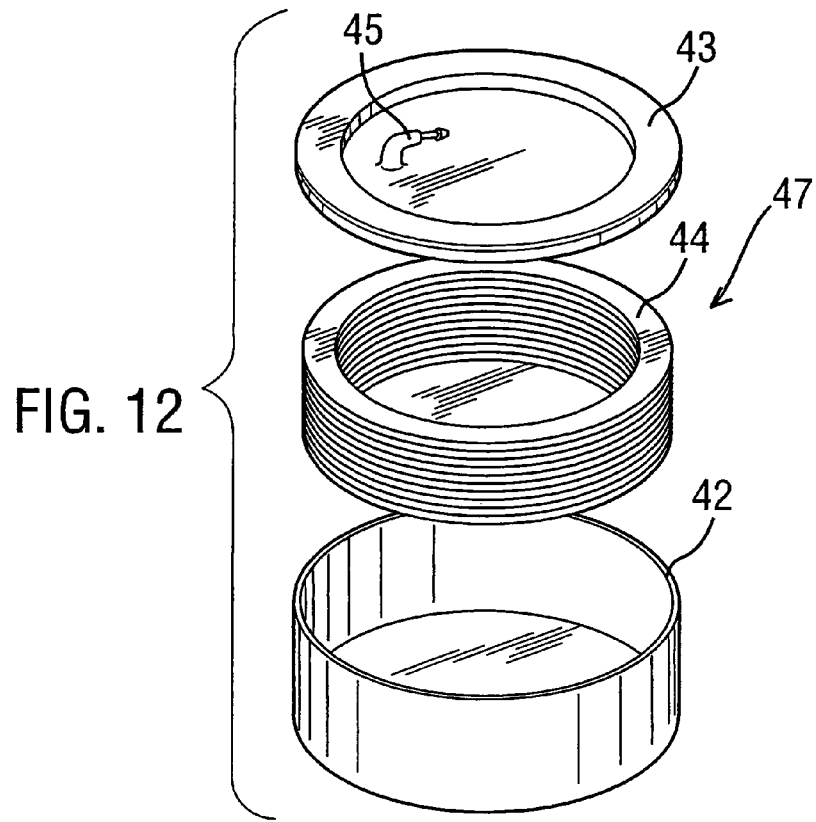
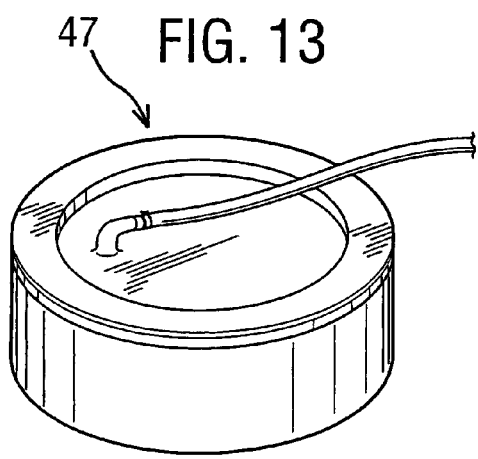
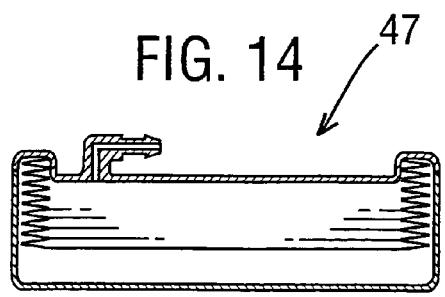

IMPLANTABLE DRUG DELIVERY PUMP

CROSS-REFERENCE TO RELATED APPLICATIONS

This is a Continuation Application of U.S. patent application Ser. No. 10/427,506 filed Apr. 30, 2003 now abandoned, which claims priority to UK Application Serial No. 0209904.2 filed Apr. 30, 2002, both of which are incorporated herein by reference.

BACKGROUND OF THE INVENTION

1. Technical Field

The present invention relates to an implantable drug delivery pump, a drug reservoir unit, and an implantable drug delivery system. Such pumps, units, or systems may be refilled with the drug, typically by percutaneous drug injections into reservoirs via body tissue.

2. Background Art

Implantable drug delivery systems may be used for systemic or local delivery of drugs. Examples of systemic drug delivery include the regulated infusion of insulin into the body tissues for the treatment of diabetes and the infusion of Apomorphine for the treatment of advanced Parkinson's disease. The local delivery of drugs or therapeutic agents has particular application to the treatment of neurological conditions where the blood brain barrier prevents many systemically administered drugs from reaching the desired target, or where the delivery of drugs or therapeutic agents to targets other than the desired target may produce unacceptable side effects. Examples of local drug delivery into the cerebrospinal fluid that surrounds the spinal cord and brain include the intrathecal delivery of opioids for chronic pain control and the intrathecal delivery of baclofen for the treatment of spasticity. Drugs and therapeutic agents may be also delivered directly into the brain parenchyma via a catheter whose discharge portion lies adjacent to a predetermined target. Examples of this type of therapy include the infusion of gamma-amino-butyric acid agonists into an epileptic focus or pathway that will block its transmission, the delivery of cytotoxic agents directly into a brain tumor, and the infusion of neurotrophic agents for the protection and repair of failing or damaged nerve cells.

Intraparenchymal delivery of neurotrophins may be used to treat a variety of neurodegenerative disorders including Parkinson's disease, Alzheimer's disease and Amyotrophic Lateral Sclerosis, and may be also useful in stimulating the repair of damaged neural tissue after injury from trauma, stroke or inflammation.

Examples of drug delivery pumps are shown, for example, in U.S. Pat. No. 4,013,074 and U.S. Pat. No. 4,692,147, each of which describe drug filled reservoirs located within the pump, which are positioned within a housing that contains a gas such that when the reservoir is filled, the gas is compressed which in turn, provides the pressure to empty the reservoir. In particular, U.S. Pat. No. 4,692,147 describes a battery powered motor driven pump, which may be seen in FIGS. 1 to 3 of this specification. From FIG. 1, it will be understood that the pump 1 is implanted subcutaneously, and that it may be refilled via a refill port 2, which may be accessed by percutaneous drug injection. The pump 1 includes an outlet port 3 through which the drug is pumped to an outlet tube 4.

Referring to FIG. 2, it will be seen that the pump 1 includes a pump unit 5 beneath which is located a dish 6 which defines a reservoir. The pump unit 5 and the dish 6 are enclosed by top and bottom parts of a housing 7, 8. The pump unit 5 includes the drug refill port 2, batteries 9, and a roller pump 10.

FIG. 3 shows the roller pump 10 in more detail. Within the roller pump 10 is a rotor 11 mounted for rotation within a pump housing 12. The rotor 11 includes two diametrically opposite arms, each of which terminates in a roller 13 which engages with a length of tubing 14 such that, as it rotates, the rollers 13 at the end of the rotor arms crush the length of tubing to drive the fluid through the length of tubing 14 as the rotor 11 rotates from an inlet 15 to an outlet 16. A flexible sheet 17 overlies the length of tubing 14, over which the roller 13 moves, the sheet 17 acting as a shim between the length of tubing 14 and the rollers 13. An example of a pump arranged in a similar way to that described in U.S. Pat. No. 4,692,147 is the Synchromed EL pump (Medtronic Inc, Minneapolis).

Passive drug reservoirs are also known where regulators control the flow of fluid exiting a gas-pressurized drug filled reservoir. The energy required to deliver the drug to its target is imparted to the pump upon filling the reservoir and compressing the gas. The regulators are either coiled lengths of fine bore tubing or etched fluid conducting channels in a chip. Passive drug dispensers are less reliable in delivering the desired dose than mechanical dispensers since the dose of drug delivered by passive dispenser depends upon the pressure in the drug filled reservoir, the resistance set by regulator, the resistance in the pump to catheter tubing, the resistance in the catheter, the pressure applied by the tissue (tissue turgor) at the catheter's delivery port, as well as the viscosity of the fluid being delivered. With passive drug dispensers, the accuracy of drug delivery is least reliable when the flow rates are low and the regulator needs to impart a high resistance. In these circumstances, small changes in the viscosity will have a significant bearing on the flow rate and the dose of drug delivered. For the delivery of neurotrophic factors into the brain parenchyma, low flow rates of the order of 1-10 μl per hour are desirable and because neurotrophic factors are proteins in suspension. They will impart a higher viscosity than crystalloid drugs and alter the flow rate accordingly. Proteins in suspension may also have a tendency to deposit within the fine tubing or etched channels of the passive regulator and further influence the flow rate.

Thus, for the delivery of proteinaceous drugs and particularly the intraparenchymal delivery of neurotrophic factors to the brain, battery powered mechanical dispensers are preferable to passive dispensers. For safety as well as the ability to alter the dosing regimen as required, a pump that can be controlled by telemetry is also desirable. Of the battery powered mechanical pumps described in the prior art that are programmable using telemetry, all have the drug dispenser unit containing the battery or batteries, motor, dispensing actuator and electronics for programming housed with the pressurized drug filled reservoir. This tends to make the pumps bulky for subcutaneous implantation because the reservoir alone may contain between 10 and 24 ml. The Synchromed EL pump contains a reservoir of 16 ml, is cylindrical in shape and has a diameter of 7 cm and a height of 2.9 cm. Its size means that it is necessary to implant such pumps subcutaneously in the anterior abdominal wall where they are least obtrusive. Nevertheless, when implanted in thin patients, the bulk of the pump can cause considerable inconvenience and discomfort. If, on the other hand, the pump is deeply placed in the subcutaneous fat of an obese patient, finding the refill port can be also problematic. Minimizing the volume of the reservoir of the pump has the disadvantage that the pump will require percutaneous refilling more frequently, thereby increasing the necessity for the patient to attend a clinic, and increasing the risk of introducing infection.

To treat neurodegenerative disorders, brain injury or other disorders with neurotrophins, it may be desirable to deliver them to more than one neurological site in the central nervous system, preferably the brain or spinal cord, most preferably the brain. For example, Parkinson's disease may be treated by infusing glial-derived neurotrophic factor (GDNF) delivered by one or more catheters implanted bilaterally into each dorsal putamen. Similarly, Alzheimer's disease may be treated by infusing nerve growth factor delivered by one or more catheters implanted bilaterally into each nucleus basalis.

Delivering the drug to multiple sites by implanting multiple pumps of the types described in the prior art would be unacceptable, and only U.S. Pat. No. 5,752,930 discloses the delivery of a drug from a single pump to multiple sites. This teaches the fluid delivery through a single catheter with multiple ports. Such a device will not facilitate drug infusion bilaterally into the brain or to other sites other than those along the axis of the implanted catheter.

Each of the prior art documents referred to above are herein incorporated in their entirety by this reference.

Two or more catheters could be connected to the outflow tubing from a single pump via a single input/multiple output connector. Such an arrangement would not guarantee an even distribution of drug to each catheter because fluid will flow primarily down the catheter offering the least resistance. To overcome this, the connector would have to act as a regulator to ensure that resistance is overcome. This will put a great demand on the pump and will increase the stress on joints between the pump and the connector. For very low flow rates, such as one or two µl per hour, the outflow ports in such a connector acting as a regulator will need to be extremely small.

SUMMARY OF THE INVENTION

According to a first aspect of the present invention, there is provided an implantable drug delivery pump comprising a metering pump including a rotor, at least two lengths of tubing against which the rotor is movable to urge the drug therethrough, and an outlet port associated with each of the at least two lengths of tubing. In this way, the drug can be pumped from the pump to multiple targets in even quantities. In this specification, references are made to the pumping and delivery of drugs, and such references include all therapeutic agents including such substances as proteins, cytokines, neurotrophic agents, toxins to destroy cancerous tissue and therapeutic markers to assist in imaging targets.

The invention allows a drug to be delivered to more than one site. This may be for the reasons outlined above that both sides of the brain need to be treated in conditions such as Parkinson's disease and Alzheimer's disease, or because multiple sites of delivery within a target volume may be necessary to optimize the distribution of the therapeutic agent. It is generally the rule that equal volumes of the therapeutic agent will need to be delivered to each site. The pump of the present invention achieves this with the advantage of being both compact and energy efficient.

It is preferred that the metering pump includes a housing having an interior wall, and arranged such that each of the lengths of tubing is arranged between the rotor and the interior wall of the housing, whereby the rotor urges the drug through the length of tubing.

It is also preferred that the rotor includes two rotor arms, and in some circumstances it is advantageous to include three rotor arms, or even four or more rotor arms.

The number of lengths of tubing that are included depends on the number of targets to which it is intended to deliver the drug. In some circumstances, it is preferred to include between three and six lengths of tubing.

According to a preferred embodiment, the pump includes a motor for moving the rotor, and this motor is most preferably a stepper motor.

It is also advantageous for the rotor to carry a roller for engagement with the length of tubing. Lower resistance and reduced wear result from the use of the roller.

In an alternative embodiment, the lengths of tubing might be arranged to be of different diameters such that different flow rates are generated from different outlet ports. This will be of particular value where the treatment of different targets require different volumes of the drug to be delivered.

According to a second aspect of the invention, there is provided a drug reservoir unit comprising an outer housing; a reservoir container disposed within the outer housing and arranged to be variable in volume; and a port through which a drug may fill or exit from the reservoir container leading to a separately located pump. The reference to a separately located pump in this specification makes it clear that the reservoir unit is not an integral part of the pump. In one embodiment, the reservoir container is in part defined by the outer housing, and it is preferred that in this case, the reservoir container is defined at least in part by a bellows.

In a second embodiment, the reservoir container is defined at least in part by a resilient bladder. The bladder is preferably constructed from two resilient discs joined in face-to-face relationship at their peripheries. In such a case, the outer housing is advantageously dome-shaped. It should also be noted that the reservoir unit could include a refill port.

According to a third aspect of the present invention, there is provided an implantable drug delivery system comprising a drug reservoir unit for holding a drug, a pump unit disposed remotely from the drug reservoir unit and including a metering pump arranged for pumping the drug from the drug reservoir unit to a delivery zone; and a supply tube disposed between the pump unit and the drug reservoir unit.

By locating the pump unit and the drug reservoir separately, the pump unit will be more compact, and may allow a surgeon to implant it in a range of alternative locations where it is comfortable and access to the refill port is improved. Also, by locating the drug reservoir unit separately, the unit may be arranged to hold a greater volume of the drug, thereby reducing the number of clinic visits for percutaneous refilling, and also reducing the risk of introducing infection. A limitation on the size of the reservoir is the stability of the drug because there is no valve in the reservoir being of greater capacity than the total volume of a drug that will be delivered at the prescribed rate before the drug begins to degrade.

The reservoir should be preferably located subcutaneously over the abdominal wall and most preferably within the rectus sheath, overlying the rectus muscles of the anterior abdominal wall because this will tend to reduce its prominence.

For drug delivery to the brain, it is preferable to position the pump close to the head. This minimizes the length over which the pump outflow tubing needs to be tunneled subcutaneously, reduces the dead space in the tubing and also reduces the resistance to the flow of fluid, thereby improving energy efficiency for pump.

According to preferred embodiments, an outlet tube leads from the pump unit to the delivery zone. It is preferred that a plurality of outlet tubes lead to a plurality of delivery zones, so that treatment is optimized.

It is also preferred that the pump unit further includes a drug refill port through which the reservoir is filled. This is preferred because the pump unit may be unobtrusively implanted in the subclavicular region while the bulkier drug reservoir may be implanted in the abdominal wall. Whereas the anterior abdominal wall may contain considerable subcutaneous fatty tissue, the subclavicular region has comparatively little subcutaneous fat and so if the drug port is housed with the drug dispenser, it should be relatively easy to palpate percutaneously.

It is least intrusive, and therefore preferred, if the drug refill port is arranged to fill the reservoir via the supply tube. Filling will result in the flow of the drug through the supply tube in the opposite direction to the supply of the drug to the pump unit during drug delivery.

It is preferred that the system further comprise one or more neurosurgical catheters for delivering the drug to delivery zones.

BRIEF DESCRIPTION OF THE DRAWINGS

Other advantages of the present invention are readily appreciated as the same becomes better understood by reference to the following detailed description when considered in connection with the accompanying drawings wherein:

FIG. 2 is an exploded view of the prior art device shown in FIG. 1;

FIG. 12 is an exploded view of a drug reservoir unit;

FIG. 13 is a perspective view of the drug reservoir unit shown in FIG. 12;

FIG. 14 is a sectional view of the drug reservoir shown in FIGS. 12 and 13;

DETAILED DESCRIPTION OF THE INVENTION

Figure 4:
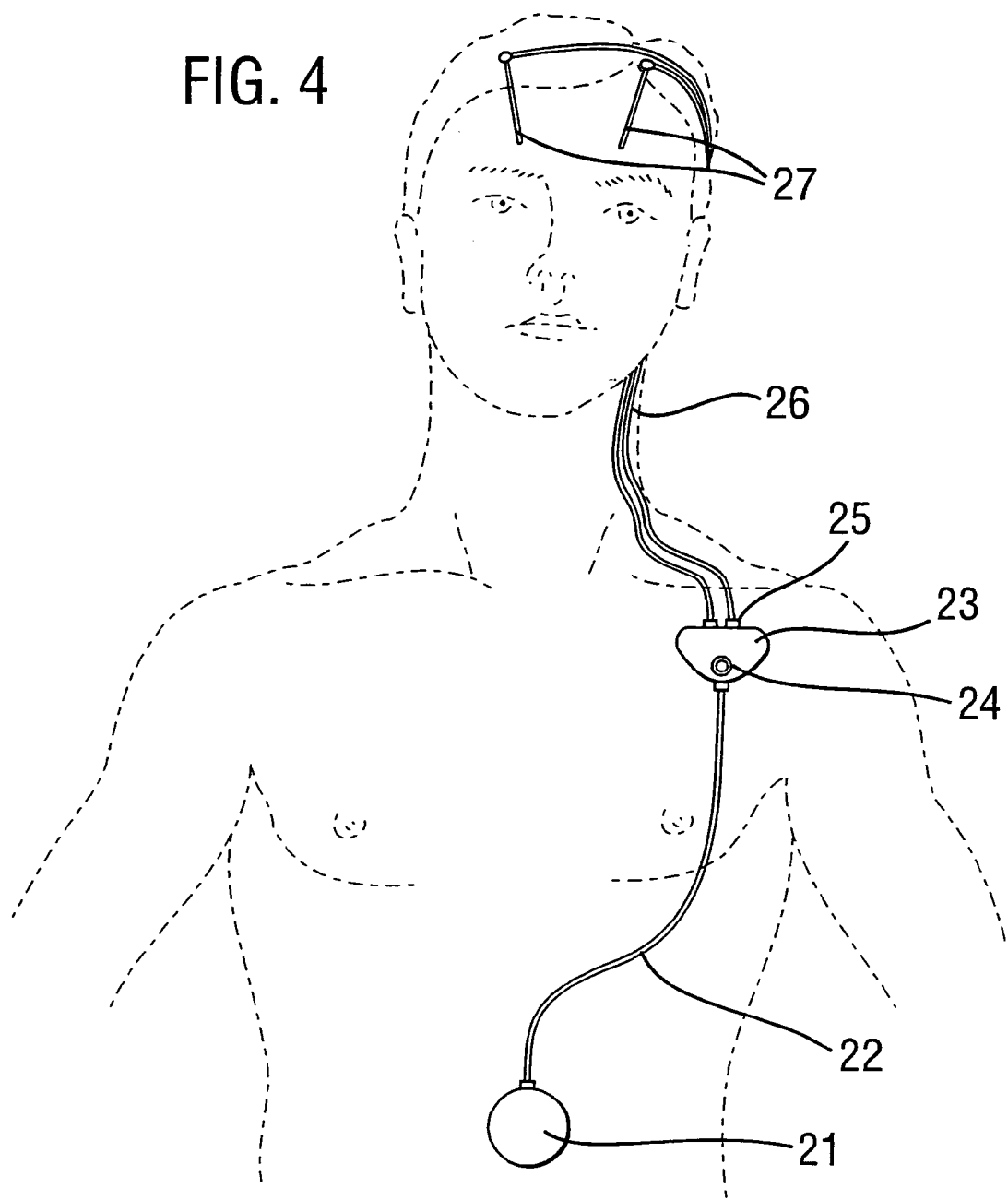
FIG. 4 is a schematic view showing an implantable drug delivery system according to the present invention.

FIG. 4 is a schematic view showing an implantable drug delivery system. A reservoir unit 21 is shown implanted subcutaneously over the anterior abdominal wall of a patient, and preferably within the rectus sheath anterior to the rectus muscle. The reservoir unit 21 has the purpose of holding a volume of a drug for infusion, and since the unit 21 is quite bulky in order to retain as much drug as possible, such a location is very suitable. Leading from the reservoir unit 21 is a supply tube 22, which leads to a pump unit 23. The supply tube 22 is tunneled subcutaneously between the reservoir unit 21 and the pump unit 23. The pump unit 23 is subcutaneously implanted in the subclavicular region. Implantation at this location is possible since the pump unit 23 is compact, made possible by the remote location of the reservoir unit 21. This location for the pump unit 23 is particularly advantageous since it should not prove to be inconvenient or uncomfortable to the patient, and yet it is close enough to the surface of the body that percutaneous refilling is relatively easy. It will be seen from FIG. 4 that the pump unit 23 includes a refill port 24 on its front surface through which it is easy to palpate. The pump unit 23 includes one or more outlet ports 25 from which the drug is pumped into one or more outlet tubes. The outlet tubes 26 lead to intraparenchymal catheters 27 which are implanted in the brain of the patient.

Intraparenchymal catheters are known in the field of neurosurgery for infusing drugs to particular parts of the brain. The catheters are rigid tubes, which are inserted stereotactically and secured to the skull with their distal ends in the vicinity of targets to be treated within the brain. The intraparenchymal catheters 27 are connected to the outlet tubes 26 which are tunneled subcutaneously through the scalp and neck.

It will be understood that, while there are often major advantages to delivering a drug to more than one target within the brain, the advantages of locating the reservoir unit 21 and the pump unit 23 separately can be also extremely advantageous where a drug is delivered to just one target.

Once the drug delivery system has been installed in the body of the patient, the reservoir unit 21 may be filled by inserting a hypodermic needle through the skin of the patient through the refill port 24. The drug can be then inserted into the pump unit 23 where it is directed through the supply tube 22 to the reservoir unit 21. The reservoir unit 21 is arranged such that the drug contained therein is held there under a pressure, which urges the drug upwards to the pump unit 23. This way, the pump unit 23 merely pumps the drug from the pump unit 23 to the target, and does not have to draw the drug from the reservoir unit 21. This will clearly reduce the power consumed by the pump unit 23 and assist in preserving battery life. The speed and operation of the pump unit 23 can be preset, although it is preferable for it to be telemetrically controlled from outside of the patient's body. During pumping, the drug is pumped at a steady rate from the outlet ports 25, via the outlet tubes 26 to the neurosurgical catheters 27, where the drug is released at the target to be treated. In certain applications, the flow rate of the drug being administered may be of the order of one to ten μl per hour.

Figure 1:
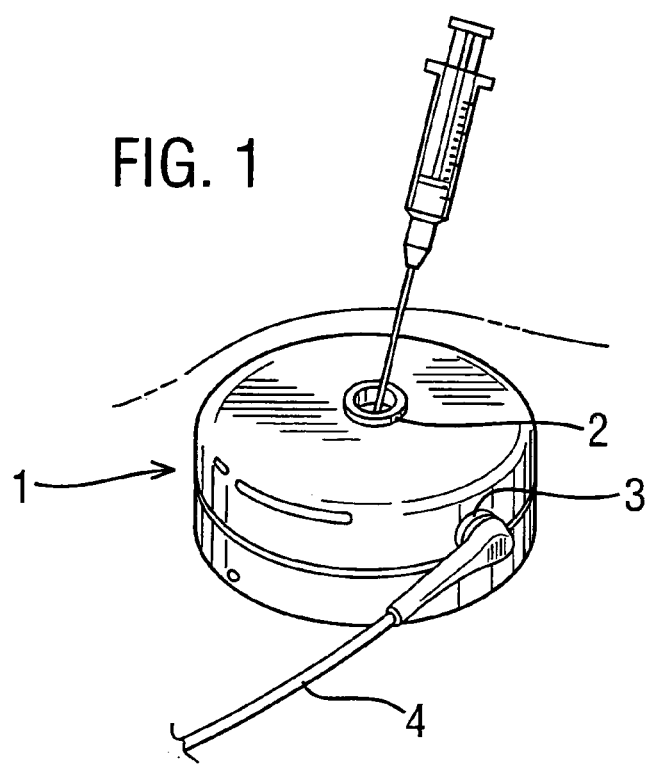
FIG. 1 is a prospective view of a prior art device.
Figure 3:
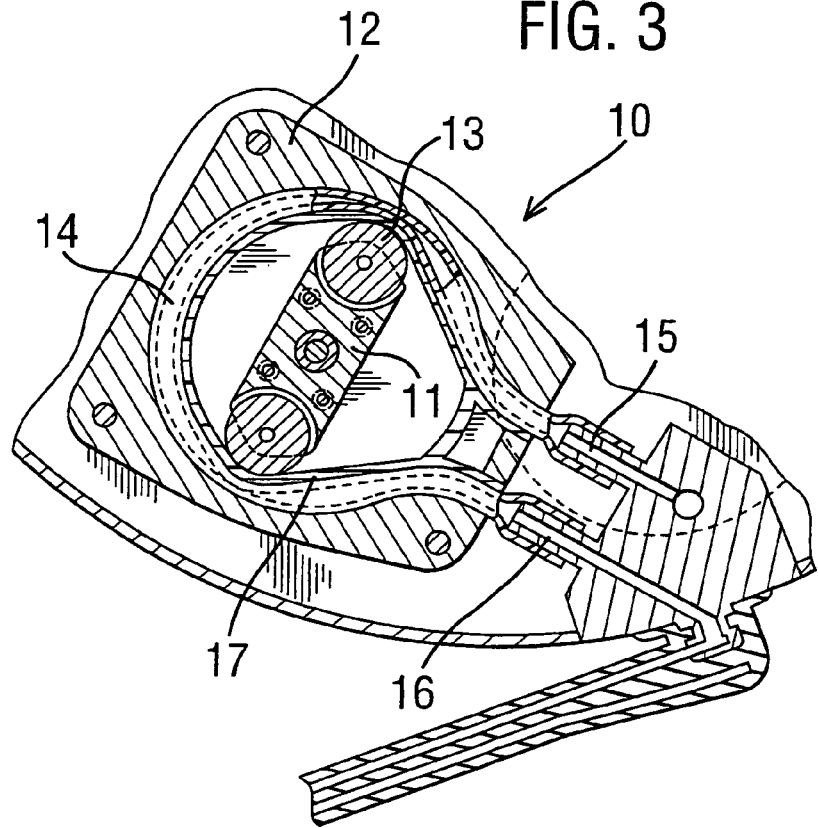
FIG. 3 is a cross-sectional plan view of the prior art device shown in FIG. 1.
Figure 9:
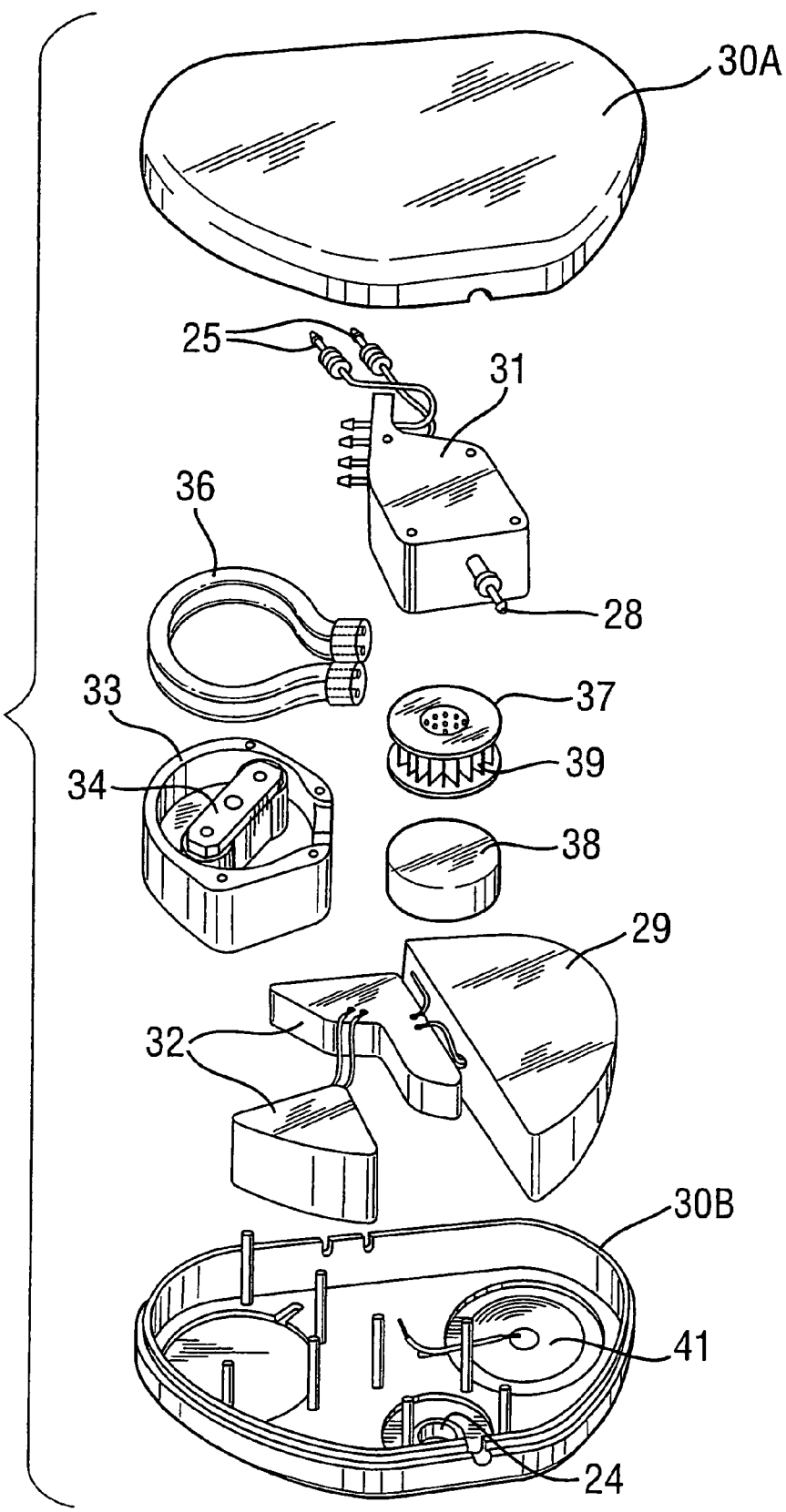
FIG. 9 is a more fully exploded view of the pump unit shown in FIGS. 5 to 8.

Referring to FIGS. 5 to 9, the pump unit 23 is shown including the outlet ports 25 in the form of connectors for connecting to lengths of tubing. The pump unit 23 also includes an inlet port 28 in the form of a connector, whereby the supply tube 22 may be connected. Within the pump unit 23 is located a battery 29, a roller pump 30, a refill port/filter unit 31 and two electronics modules 32. From FIG. 5 it will be seen that the roller pump 30 includes a housing 33 having a curved interior wall, a rotor 34 rotatable within the housing and arranged with two diametrically opposite rotor arms each of which ends in a roller 35. A dual length of tubing 36 is disposed against the curved interior wall of the housing 33 such that the rollers 35 crush the tubing 36 against the interior wall of the housing 33. When the rotor 34 is rotated, the rollers 35 roll over the dual length of tubing 36 so as to urge any fluid within the tubing therethrough. It is this, which generates the pumping of fluids through the drug delivery system. Although not shown in the drawings, a shim or flexible sheet is disposed over the tubing 36 such that the rollers 35 do not bear directly on the tubing 36, but on the shim, thereby reducing wear on the tubing 36. An example of a shim is shown in FIG. 3. The rotor 34 is rotated by a stepper motor (not shown), although other suitable motors could be used. It will be understood that a dual length of tubing 36 is one where two tubes extend side by side, as is seen in FIG. 9.

Figure 5:
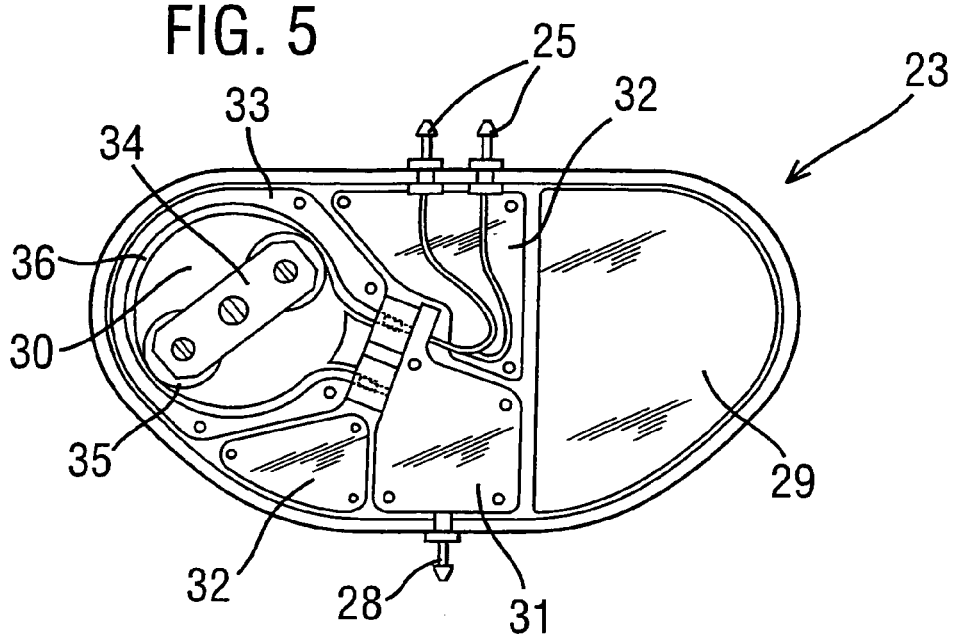
FIG. 5 is a rear view of a pump unit according to the present invention, with part of the casing removed to reveal the interior of the unit.
Figure 6:
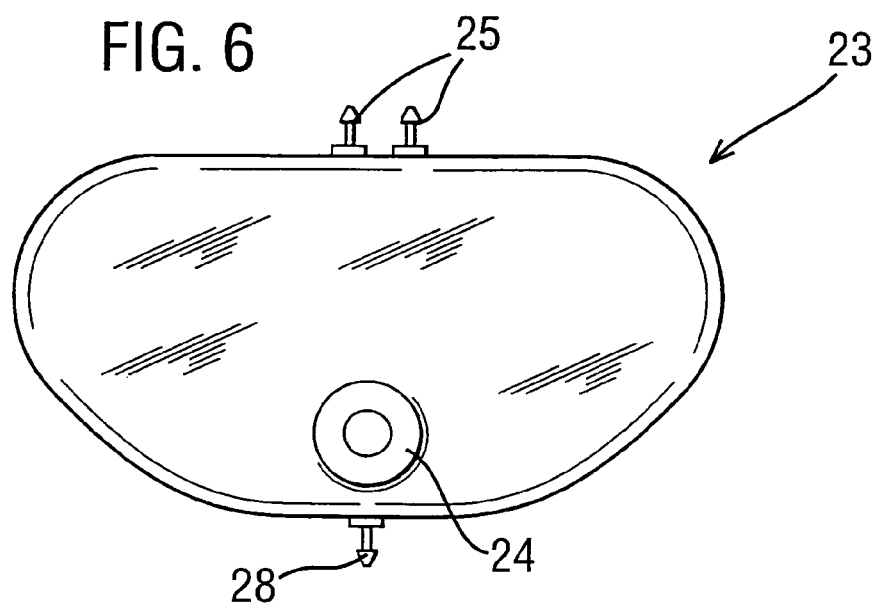
FIG. 6 is a front view of the pump unit shown in FIG. 5, but with the casing in place.
Figure 7:
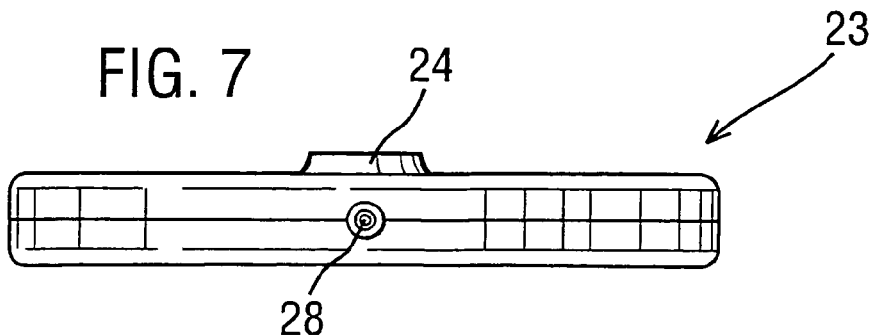
FIG. 7 is an underside view of the pump unit of FIGS. 5 and 6.
Figure 8:
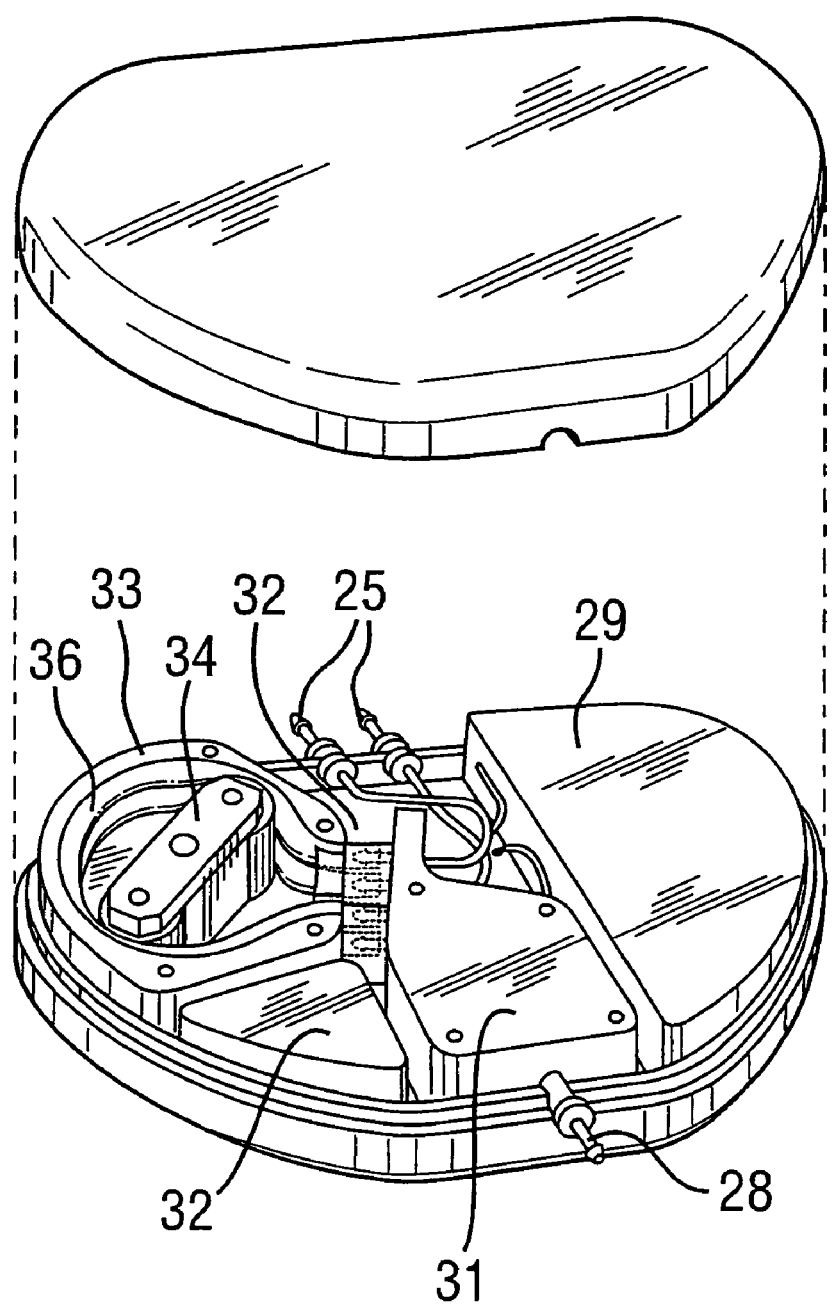
FIG. 8 is a partially exploded view of the pump unit of FIGS. 5 to 7.

It will be appreciated that the inlet port 28 leads fluid from the reservoir unit 21 via the supply tube 22 into the roller pump 30. Since the length of tubing 36 within the roller pump 30 is dualled, this means that one inlet line can be converted to two outlet lines. In this regard, it will be seen that there are two outlet ports 25, each connected to one of the lengths of tubing 36 passing through the roller pump 30. In FIG. 5, only one of the lengths of tubing 36 through the roller pump 30 can be seen since the length of tubing will be stacked axially with respect to the axis of rotation of the rotor, but the tubing 36 is best seen in FIG. 9. Of course, the use of two lengths of tubing 36 means that the same volume of a drug will be delivered to two different targets. Of course, more lengths of tubing may be incorporated here, each of which is acted upon by the roller 35 of the rotor 34 in order to pump the drug to each site to which it is desired to pump the drug. In fact, if different sites required different volume of the drug to be delivered to them, the length of tubing 36 passing through the roller pump 30 can be arranged to have different internal diameters, thereby allowing pumping at different rates through different lengths of tubing. Further details of the refill port 24 and the filler unit will be described later in the specification.

FIG. 9 shows a more exploded view of the pump unit. It will be seen that in alignment with the refill port 24 is a filter element 37 and a silicone rubber seal 38. The seal 38 closes the port 24 so that nothing can pass either way through the port 24 unless it is inserted using a hypodermic needle from outside. The seal is able to form a seal around the hypodermic needle during filling of the system, and once the needle has been removed, the hole that the needle made will be securely sealed closed again in order to prevent foreign bodies from entering the system, and to prevent the drug from escaping from within the system.

During filling, the tip of the hypodermic needle is located within the central well of the filter element 37, and during filling, the drug must pass through a cylindrical bacterial filter 39 that is arranged around the outside of the filter element, and is, in this case, fluted. The filter element is arranged like a reel.

During filling, the drug from the hypodermic needle is forced through the fluted bacteriological filter 39 and is directed down through the supply tube 22 into the reservoir unit 21. The filter prevents any particulate matter within the drug that is inserted from being passed into the rest of the system, the particulate matter being retained within the filter element 37. The particulate matter can be, for example, fragments of skin, hair or bacteria. Implantable pumps require a filter to screen out the particulate matter. Fine filters provide resistance to the flow of fluid, and to reduce this, the surface area is maximized. Whereas it is known to use large discs of porous material through which the fluid is passed, this necessarily occupies a relatively large space where space is at a premium. The filter in the present invention is very compact and is positioned at the refill port rather than between the reservoir and the pump, and so prevents any particulate matter from entering the reservoir in the first place. When the system is emptied by aspirating through the refill port, particulate matter may be flushed out of the filter, and so help clean it. The resistance offered by the filter in the present invention is overcome when fluid is injected into the refill port and avoids the increase in demand on the pressurized reservoir to overcome the filter resistance, which is inherent in the teaching of the prior art. The increased resistance in the prior art may contribute to a fall off in the pressure of fluid delivery to the pump as the reservoir becomes depleted, and may contribute to inaccuracies in drug delivery. The bacterial filter is intended to have a four micron mesh size.

The pump unit is closed by a lower casing 30A and an upper casing 30B, each of which is made of titanium. The various components shown in FIG. 9 are spot welded to pins located within the upper casing 30B. The refill port 24 is pressed onto the interior surface of the upper casing 30B prior to laser welding the two halves of the casing together.

In the upper casing 30B, an alarm unit 41 can be seen which might be used to draw the patient's attention to some potential problem with the system.

Figure 10:
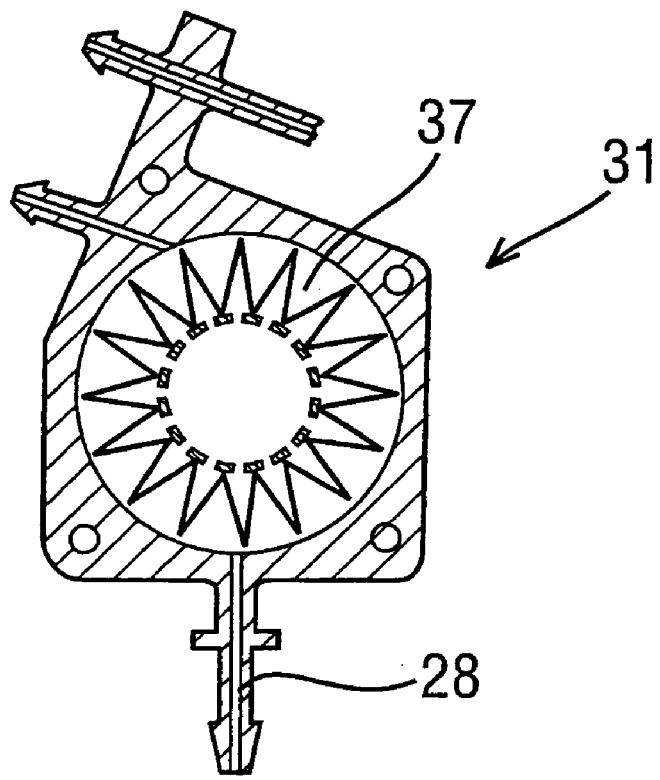
FIG. 10 is a sectional view of a filter unit of the pump unit viewed from the front.
Figure 11:
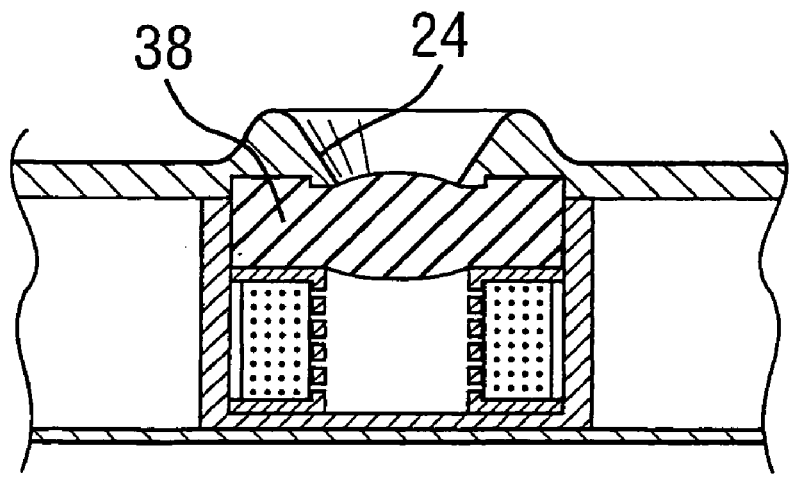
FIG. 11 is a sectional view of part of the filter unit as viewed from below.

FIGS. 10 and 11 show the filter unit 31 in more detail with the filter element 37 mounted in place. The seal 38 can clearly be seen in FIG. 11, through which the drug is injected. It can also be seen that the inlet port 28 extends from the filter unit 31 so that the drug, on its way to the patient from the reservoir unit 21, passes through the filter unit 31 on its way to the roller pump 30.

FIGS. 12, 13, and 14 show a first design of a reservoir unit 47. The reservoir unit includes a top casing 42, which is cylindrical in shape, closed at one end, a bottom plate arranged to close the open top of the top casing 42, and bellows 44 located within the top casing and bottom plate. The bottom plate 43 includes an inlet/outlet port 45 through which the drug passes to fill the reservoir unit, and to lead via the supply tube 22 to the pump unit 23. The bottom plate 43 and bellows 44 define a sealed fluid reservoir. The space outside of the fluid reservoir, but within the housing, is also sealed and contains a small amount of fluorocarbon fluid or other volatile fluid that will provide positive pressure against the bellows sufficient to force the liquid out of the reservoir via the inlet/outlet port 45 towards the pump 23. The reservoir unit may be of any suitable size depending on the requirements of the individual patient. Typical volumes of the reservoir may be 10 ml, 20 ml or 30 ml. The reservoir would preferably have a low profile with rounded edges in order to be as unobtrusive as possible to the patient. The top case in 42 and the bottom plate 43 are titanium.

Figure 15:
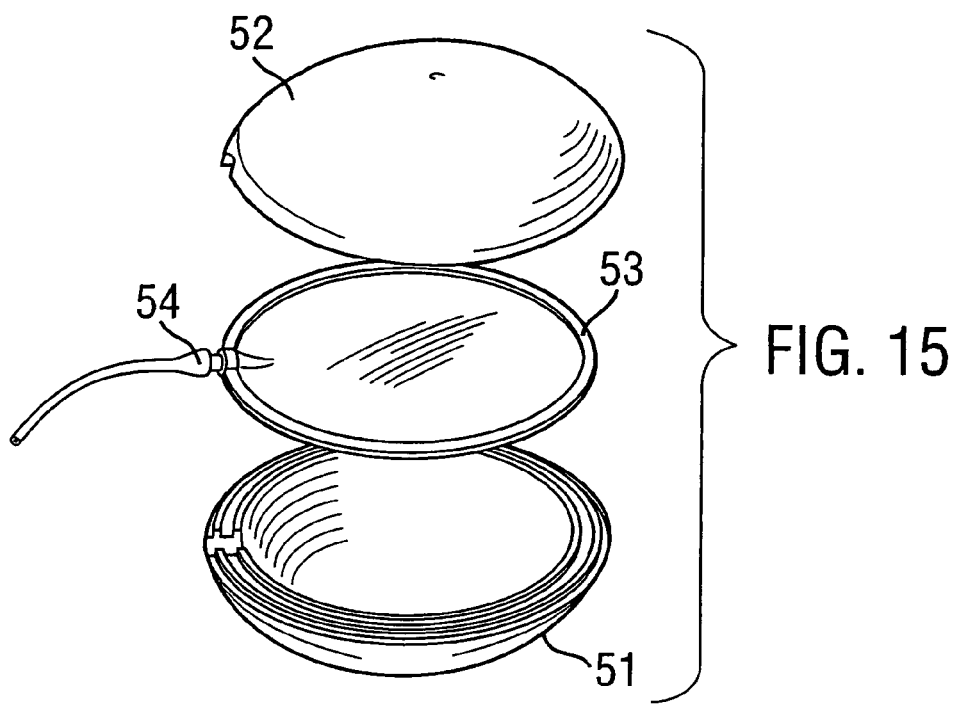
FIG. 15 is an exploded view of an alternative form of drug reservoir according to the present invention.
Figure 16:
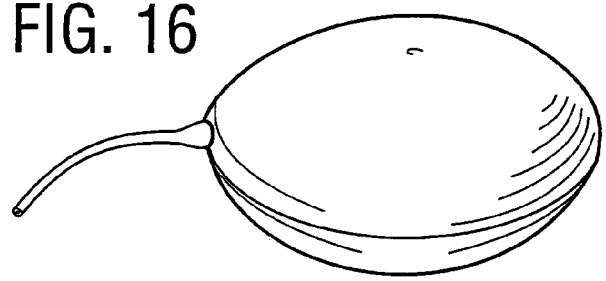
FIG. 16 is a perspective view of the reservoir of FIG. 15.
Figure 17:
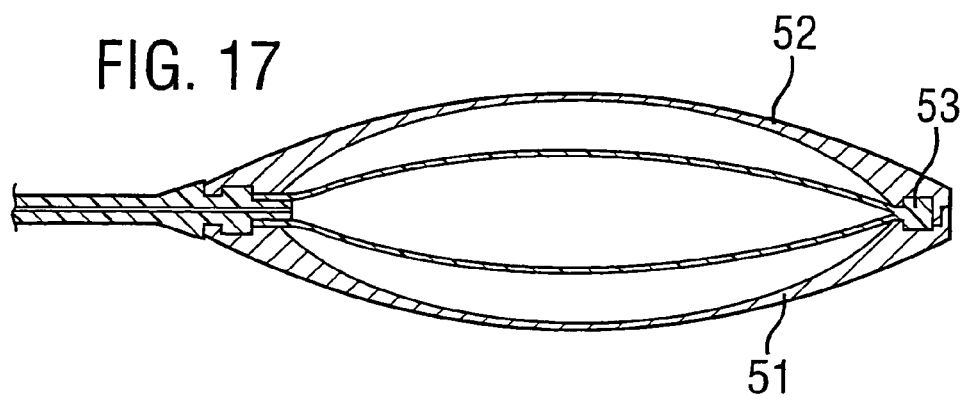
FIG. 17 is a sectional view through the reservoir unit shown in FIGS. 15 and 16.

FIGS. 15, 16, and 17 show a second embodiment of reservoir. This reservoir includes a domed lower casing 51, a domed upper casing 52 and a resilient bladder 53 disposed therebetween. The bladder 53 is constructed from two polyurethane discs placed face-to-face and sealed around their peripheries. The bladder 53 includes an inlet/outlet port 54 for connection to the supply tube 22 leading to the pump unit 23. The space outside of the bladder, but within the casing 51, 52, is a partial vacuum. The bladder 53 has sufficient resilience to expel any drug, and the partial vacuum ensures constant outflow pressure.

The materials used for various components of the system must be those, which are most tolerable to the body of the patient in order to reduce the risk of rejection systems. It is for this reason that the casings of the pump unit and the reservoir unit are constructed from titanium, although other materials might be also suitable.

The inlet port 28 and the outlet ports 25 to the pump unit 23, and the inlet/outlet port 45, 54 of the reservoir unit are, in this embodiment, in the form of a nipple over which the various tubes must be forced and subsequently compressed by tightening a ligature, a crimped ring, a deformed washer that is compressed by a threaded encircling nut, or by other suitable means.

It will be appreciated that the modular nature of the drug delivery system means that, if the pump unit 23 were to fail, or the battery to run down, the pump unit 23 may be surgically replaced while leaving the reservoir unit 21 and the neurosurgical catheters 27 in place. The new pump unit is merely reconnected to the various tubes. Also, the modular arrangement allows a pump to be used in a system with a variety of different types and sizes of reservoir. A smaller reservoir is suitable where very low flow rates are to be used, and where the drug being used has a short storage life. Also, if the reservoir needs to be replaced, this can be done without disturbing the rest of the system. Such a modular arrangement would be just as suitable if there were only one outlet port 25 leading from the pump unit 23.

Certain drugs, which are used for delivery to parts of the body are inherently toxic, or have serious side effects. Therefore, such drugs are normally delivered in a composition including a neutralizing substance. However, the storage life of the composition tends to be much shorter than the storage life of the drug on its own. As a result, in the present invention, the drug can be stored in one reservoir, and the neutralizing substance in another, and outlets from each of the reservoirs can lead to inlets to the pump. The pump will then pump the two substances in the appropriate proportions, such that after pumping, the two substances are allowed to mix and are fed through the system to the catheter for delivery. It will be appreciated that the mixing proportions will be controlled by the sizes of the respective length of tubing passing through the pump.

As explained above, although the present embodiment includes two outlet ports 25, the roller pump 30 can be arranged such that the rotor passes over more lengths of tube in order to pump the drug to more targets within the body such as the spinal cord.

The rotor 34 in the present embodiment includes two arms, each of which terminates in a roller. However, it is possible to increase the number of rollers above two.

Since the pump unit may be controlled by non-invasive telemetry, the rate of rotation of the rotor can be adjusted to adjust the rate of which the drug is delivered.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A drug delivery system comprising:
   a drug reservoir unit for holding a drug;
   an implantable pump unit disposed remotely from the drug reservoir unit and including a pump arranged for pumping a drug from the drug reservoir unit to a plurality of delivery zones, said pump unit having a plurality of outlet ports; and
   a supply tube disposed between the pump unit and the drug reservoir unit.

2. A drug delivery system according to claim 1, wherein a plurality of outlet tubes are provided that lead from the plurality of outlet ports to the plurality of delivery zones.

3. A drug delivery system according to claim 1, wherein the pump unit includes a drug refill port through which the drug reservoir unit can be filled.

4. A drug delivery system according to claim 3, wherein the drug refill port is in fluid communication with the drug reservoir unit via the supply tube defining a fluid path.

5. A drug delivery system according to claim 3, comprising a bacterial filter disposed across a fluid path between an entrance to said drug refill port and said reservoir, wherein during filling, fluid is passed from the drug refill port to the drug reservoir unit through the bacterial filter.

6. A drug delivery system according to claim 1, comprising one or more neurosurgical catheters for delivering the drug to said deliver zones.

7. A drug delivery system according to claim 1, wherein the pump comprises a metering pump including a rotor, at least two lengths of tubing against which the rotor is moveable to urge the drug therethrough; and an outlet port associated with each of the at least two lengths of tubing.

8. A drug delivery system according to claim 1, wherein the drug reservoir unit comprises an outer housing and a reservoir container disposed within the outer housing and arranged to be variable in volume.

9. A drug delivery system according to claim 8, wherein the drug reservoir unit comprises a port through which a drug may fill or exit from the reservoir container leading to the pump unit.

10. An implantable drug delivery system comprising:
    a drug reservoir unit for holding a drug;
    a pump unit disposed remotely from the drug reservoir unit and including a metering pump arranged for pumping a drug from the reservoir unit to at least one delivery zone; and
    a supply tube disposed between the pump unit and the drug reservoir unit, the supply tube having sufficient length between the drug resevoir unit and the pump unit;
    wherein the pump unit is implantable in the subclavicular region of the human body and the drug reservoir is implantable in the abdomen of the human body.

11. An implantable drug delivery system according to claim 10, comprising one or more intraparenchymal catheters.

12. An implantable drug delivery system according to claim 11, comprising one or more outlet tubes, wherein the drug is pumped from the pump unit to the one or more intraparenchymal catheters via said one or more outlet tubes.

13. A method of implanting a drug delivery system in a human body, said drug delivery system including a drug reservoir unit for holding a drug, a pump unit disposed remotely from the drug reservoir unit and including a metering pump arranged for pumping a drug from the drug reservoir unit to one or more delivery zones and a supply tube disposed between the pump unit and the drug reservoir unit; wherein the method comprises the steps of: (i) implanting the pump unit in the subclavicular region of the human body, and (ii) implanting the drug reservoir unit in the abdomen of the human body.

14. A method according to claim 13, comprising the step (iii) of implanting one or more intraparenchymal catheters for delivering said drug to the one or more delivery zones.

15. A method according to claim 13, in which the pump unit includes one or more outlet ports and in which one or more outlet tubes are provided that lead from the pump unit to the one or more intraparenchymal catheters, wherein the method further comprises the step of subcutaneously tunneling said one or more outlet tubes through the scalp and neck.

16. A method according to claim 13, wherein the pump unit includes a refill port and step (i) further comprises implanting the pump unit such that the refill port is easily accessible percutaneously.

17. A method according to claim 13, wherein step (ii) further includes implanting the drug reservoir unit the abdominal wall.

18. A method according to claim 17, wherein step (ii) further includes implanting the drug reservoir unit within the rectus sheath, overlying the rectus muscles of the anterior abdominal wall.

19. A method according to claim 13, further comprising the step (iv) of delivering a drug to the one or more delivery zones.

20. A method according to claim 19, further defined as wherein delivering the drug to the one or more delivery zones at the rate of one to ten micro-liters per hour.

* * * * *